United States Patent
Hammon et al.

(10) Patent No.: US 7,109,328 B2
(45) Date of Patent: Sep. 19, 2006

(54) METHOD FOR PRODUCING ACRYLIC ACID

(75) Inventors: Ulrich Hammon, Mannheim (DE); Juergen Schroeder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/500,009

(22) PCT Filed: Jan. 3, 2003

(86) PCT No.: PCT/EP03/00010

§ 371 (c)(1), (2), (4) Date: Jun. 23, 2004

(87) PCT Pub. No.: WO03/057657

PCT Pub. Date: Jul. 17, 2003

(65) Prior Publication Data

US 2005/0143604 A1    Jun. 30, 2005

(30) Foreign Application Priority Data

Jan. 9, 2002  (DE) ................................ 102 00 583
Apr. 17, 2002 (DE) ................................ 102 17 121

(51) Int. Cl.
  C07D 279/18    (2006.01)
  C07C 57/02     (2006.01)
  C07C 51/42     (2006.01)

(52) U.S. Cl. .................... 544/35; 562/598; 562/600

(58) Field of Classification Search ................. None
  See application file for complete search history.

(56) References Cited

U.S. PATENT DOCUMENTS 5,322,960 A    6/1994  Sakamoto et al.
6,210,536 B1   4/2001  Grossi et al.
6,676,849 B1 * 1/2004  DeMassa ............... 252/182.31

FOREIGN PATENT DOCUMENTS

DE  100 64 641   6/2002
DE  102 35 847   8/2003
JP  08/073405    3/1996
WO  99/14182     3/1999

* cited by examiner

Primary Examiner—Paul A. Zucker
(74) Attorney, Agent, or Firm—Oblon, Spivak, McClelland, Maier & Neustadt, P.C.

(57) ABSTRACT

A process for the fractional condensation of a hot gas mixture which as well as acrylic acid contains at least one further condensable component in a column in the presence of at least one stabilizer comprises metering in at least a portion of the at least one stabilizer as a melt.

23 Claims, 5 Drawing Sheets

METHOD FOR PRODUCING ACRYLIC ACID

The present invention relates to a process for fractional condensation of a hot gas mixture comprising acrylic acid.

DE-A 197 40 253 and German patent application number 102 35 847.8 of Aug. 5, 2002 disclose that a reaction mixture from the catalytic gas phase oxidation to give acrylic acid can be fractionally condensed by passing it upward into a column having separating internals and condensing out the condensable components by cooling.

In the latter process (FIG. 1), preference is given to stabilizing the column in the following way:

The upper column region is stabilized by a water-soluble phenolic compound, preferably hydroquinone monomethyl ether. Stabilizer is added as a solution in dilute acid into the reflux stream or into the quench circuit.

The remaining column region is stabilized by a 0.1–1% by weight solution of phenothiazine in acrylic acid which is added in the column region where the acrylic acid concentration is 5–15% and the water concentration is 80–95%. The quantity added is determined in such a way that the phenothiazine contents in the acrylic acid fraction (medium-boiler fraction, stream 7) is 10–1000 ppm, preferably 50–500 ppm.

A disadvantage of the process described there is that the water-soluble phenolic compounds, in particular hydroquinone monomethyl ether, only have limited solubility in the dilute acid which occurs as the low-boiler fraction and is used as the solvent. This results in large quantities of stabilizer solution being required.

A further disadvantage is that the effective but sparingly water-soluble stabilizer phenothiazine cannot be metered into the upper column region owing to the high water concentration there. Only the dilute acid or acrylic acid are useful as solvents for phenothiazine. Other solvents carry extraneous materials into the system and are therefore undesirable. Phenothiazine is virtually insoluble in dilute acid. If acrylic acid were to be used as solvent, the acrylic acid used would be lost in the dilute acid.

It is an object of the present invention to provide a process for preparing acrylic acid in which phenothiazine can also be used as a stabilizer in regions of high water concentration.

We have found that this object is achieved by a process for the fractional condensation of a hot gas mixture which as well as acrylic acid contains at least one further condensable component in a column in the presence of at least one stabilizer, which comprises metering in at least a portion of the at least one stabilizer as a melt.

Figure 1:
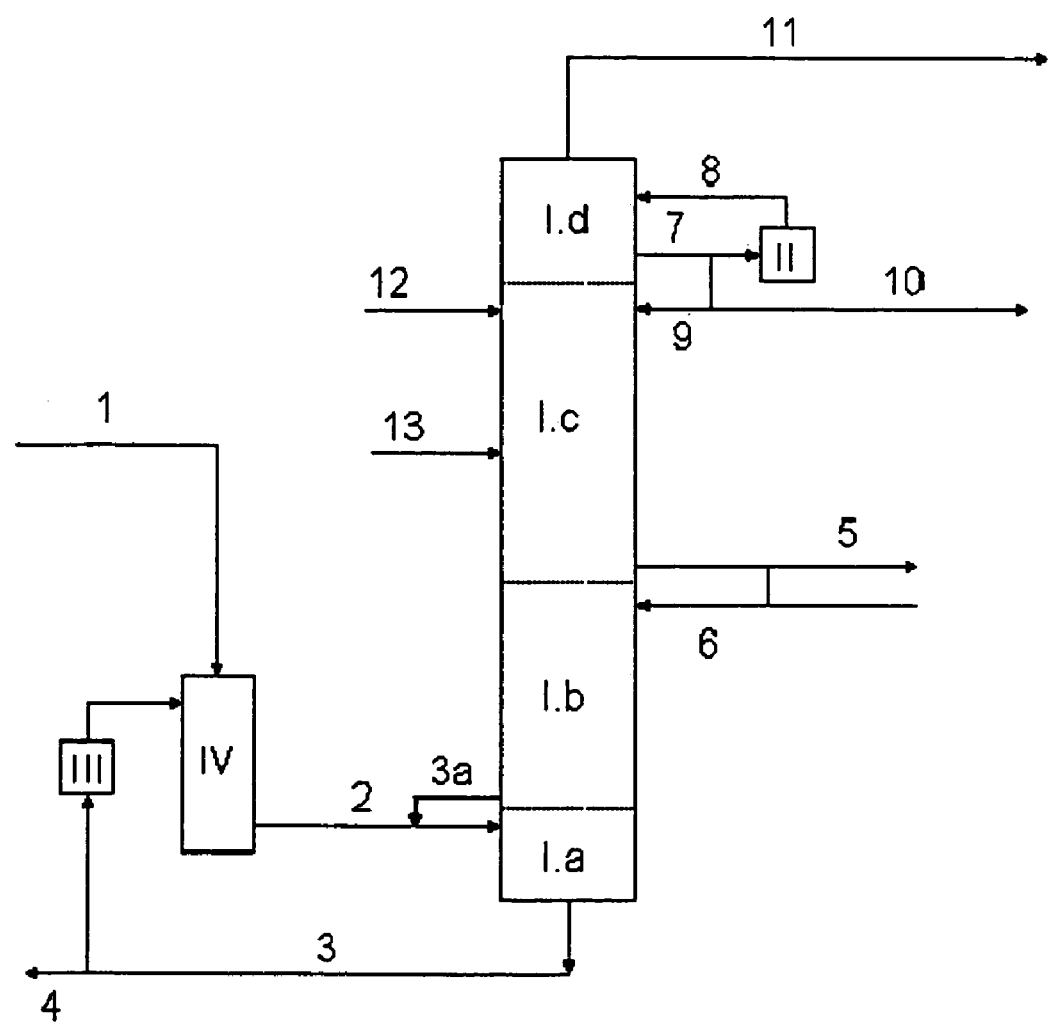
FIG. 1 shows a customary embodiment of fractional condensation of a hot gas mixture comprising acrylic acid wherein line 1 is cooled in a quench (spray cooler) IV and fed via line 2 to the bottom region I.a of the column. The coolant (unvaporized high-boiler fraction from I.a) is recycled into the quench (spray cooler) IV via line 3 in order to cool the hot gas mixture.

The process according to the invention is generally carried out as follows:

Useful hot gas mixtures include such gas mixtures as the reaction gas mixture resulting from the catalytic gas phase oxidation of $C_3$-alkanes, -alkenes, -alkanols and/or -alkanals and/or precursors thereof to give acrylic acid by known processes. Propene, propane and acrolein are particularly advantageously used for preparing acrylic acid. However, useful starting compounds for acrylic acid also include those from which the actual $C_3$ starting compound is first formed during the gas phase oxidation as an intermediate. Acrylic acid may be prepared directly from propane. When propane is used as the starting material, it may be converted by known catalytic oxidehydrogenation, homogeneous oxidehydrogenation or catalytic dehydrogenation processes to give a propene/propane mixture. Useful propene/propane mixtures also include refinery propene (about 70% propene and 30% propane) or cracker propene (about 95% propene and 5% propane). When a propene/propane mixture is used for preparing acrylic acid, propane acts as a diluent gas and/or reactant. The preparation of acrylic acid is generally carried out by diluting the starting gases with gases which are inert under the chosen reaction conditions such as nitrogen ($N_2$), $CO_2$, saturated $C_1$–$C_6$-hydrocarbons and/or steam and passing them in the mixture with oxygen ($O_2$) or an oxygen-containing gas at elevated temperatures (customarily from 200 to 450° C.) and also optionally elevated pressure over transition metal (e.g. Mo-, V-, W- and/or Fe-containing) mixed oxide catalysts and converting them oxidatively into acrylic acid. These reactions are carried out, for example, in one or more steps.

The resulting reaction gas mixture, in addition to the desired acid, contains secondary components such as unconverted acrolein and/or propene, steam, carbon monoxide, carbon dioxide, nitrogen, oxygen, acetic acid, propionic acid, formaldehyde, further aldehydes and maleic acid or maleic anhydride. Customarily, the reaction gas mixture comprises, based in each case on the total reaction gas mixture, from 1 to 30% by weight of acrylic acid, from 0.01 to 1% by weight of propene and from 0.05 to 1% by weight of acrolein, from 0.05 to 10% by weight of oxygen, from 0.01 to 3% by weight of acetic acid, from 0.01 to 2% by weight of propionic acid, from 0.05 to 1% by weight of formaldehyde, from 0.05 to 2% by weight of other aldehydes, from 0.01 to 0.5% by weight of maleic acid and maleic anhydride and the remainder comprises inert diluent gases. The inert diluent gases include in particular saturated $C_1$–$C_6$-hydrocarbons, such as methane and/or propane, and also steam, carbon oxides and nitrogen. Thus, such a gas mixture comprises, in addition to the target component acrylic acid, which condenses predominantly as the medium-boiler fraction, further compounds in the high-boiler and low-boiler range and also noncondensable fractions. The medium-boiler fraction essentially consists of the components which have, at atmospheric pressure, a boiling point in the temperature interval of, for example, from 120 to 180° C. in the case of acrylic acid, in particular in the range of +/−10° C. around that of the product of value, i.e. from about 131 to 151° C. for acrylic acid.

The reaction gas mixture may be cooled indirectly, for example using heat exchangers, which are known per se to those skilled in the art and are subject to no restriction, or directly, for example using a quench, and preferably by direct cooling.

This may be effected either in the bottom region of the column or else isolated from the column in a separate apparatus IV as shown in FIGS. 1 to 5. In this case, the hot gas mixture to be condensed having a temperature of from 200 to 400° C. from line 1 is customarily cooled in a quench IV to a temperature of from 100 to 180° C. and fed via line 2 to the bottom region I.a of the column. The coolant (unvaporized high-boiler fraction from I.a) is recycled into the quench IV via line 3 in order to cool the hot gas mixture.

Figure 2:
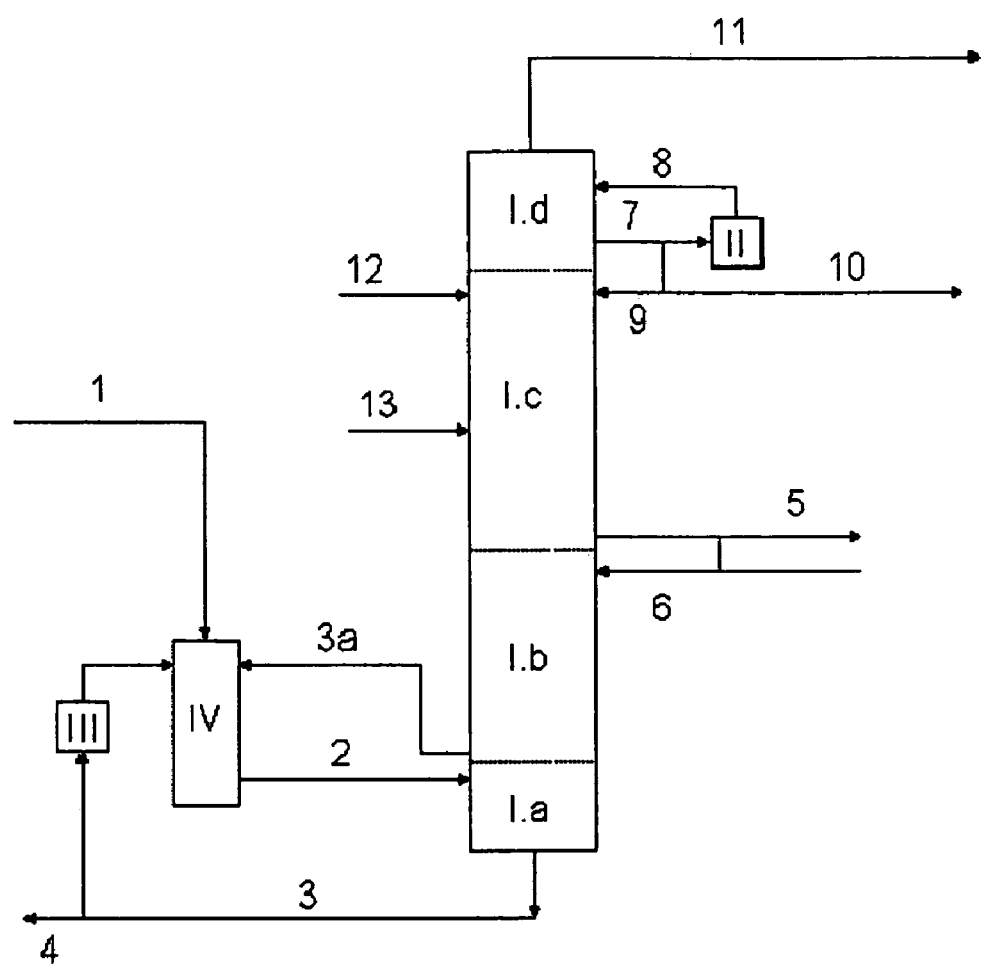
FIG. 2 shows an embodiment of fractional condensation of a hot gas mixture comprising acrylic acid wherein the high-boiler fractions of the column from sections I.a and I.b may be recycled separately into the quench. In this embodiment the fraction from I.b is directly, without heat exchangers, recycled to the spray cooler apparatus IV.

In a particular embodiment, the high-boiler fractions from I.a and I.b may be recycled separately into the quench (FIG. 2, stream 3 and stream 3a). Particular preference is given to feeding the high-boiler fraction from I.b directly, without heat exchangers, to the apparatus IV (FIG. 2, stream 3a).

A portion of the coolant from the circuit III/IV, customarily from 0.5 to 5% by weight based on 100% by weight of condensate in the sidestream, may be discharged from the process (stream 4). In the case of acrylic acid preparation, this stream generally has the following composition:

| | |
|---|---|
| 10–40% by weight | of acrylic acid |
| 10–40% by weight | of diacrylic acid |
| 5–15% by weight | of maleic acid/maleic anhydride |
| 1–3% by weight | of benzoic acid |
| 2–6% by weight | of phthalic acid/phthalic anhydride |
| remainder: | stabilizers, polymeric acrylic acid, higher molecular weight Michael addition products of acrylic acid (tri, tetraacrylic acid, etc.) |

Discharge may refer to disposal, for example by incineration, or the discharged stream may be subjected, for example, to a thermal and/or catalytic treatment, for example, for the purpose of dissociating the high-boilers, whose removed dissociation products may be fed back into the process according to the invention at any desired point.

Useful quenching devices IV include all devices for this purpose known from the prior art (for example, spray coolers, Venturi scrubbers, bubble columns or other apparatus having sprayed surfaces), and preference is given to using Venturi scrubbers or spray coolers.

Indirect cooling or heating of the quenching liquid may be effected using any conventional heat transferor or heat exchanger. Preference is given to tube bundle heat exchangers, plate heat exchangers or air coolers. The temperature of the quenching liquid after leaving the heat exchanger III is normally from 70 to 200° C., frequently from 100 to 150° C. Useful coolants include air for an appropriate air cooler and cooling liquids, in particular water, for other cooling devices.

Figure 3:
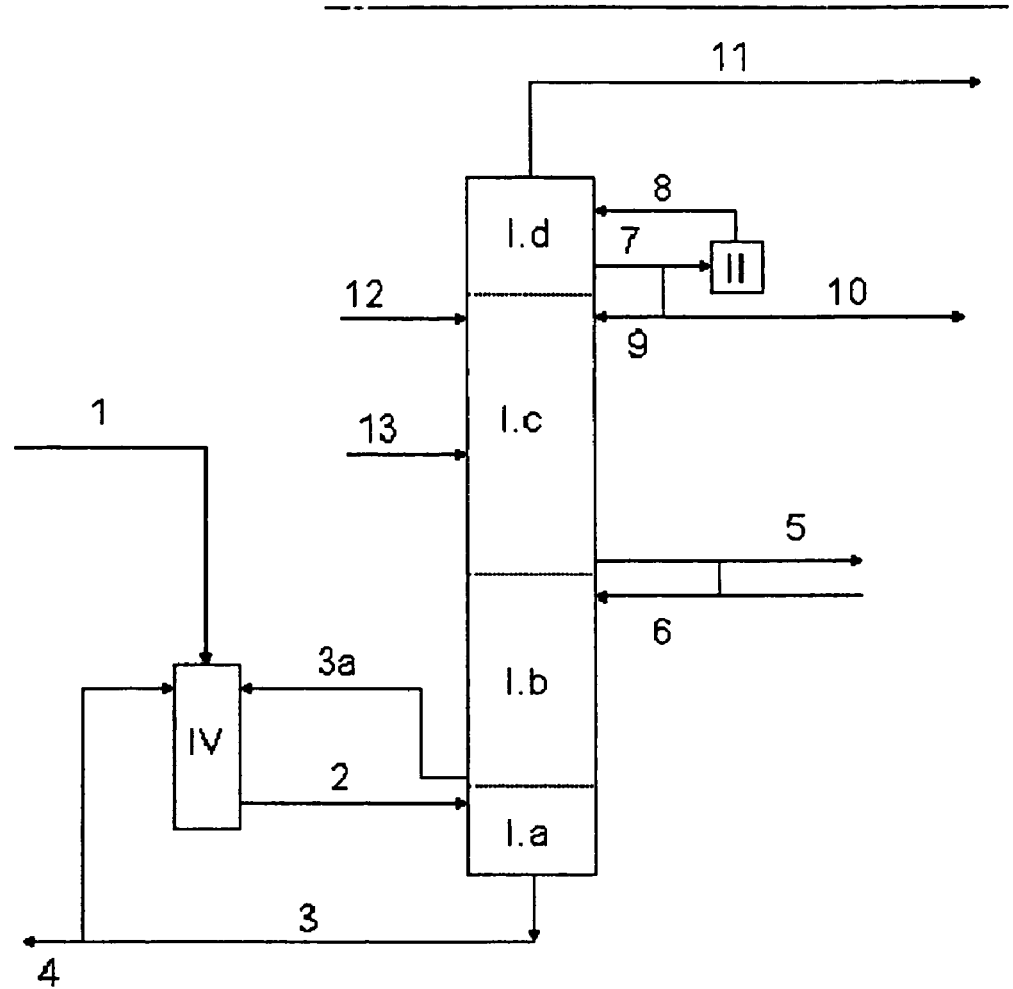
FIG. 3 shows the embodiment of FIG. 2, but in the absence of heat exchanger III.
Figure 4:
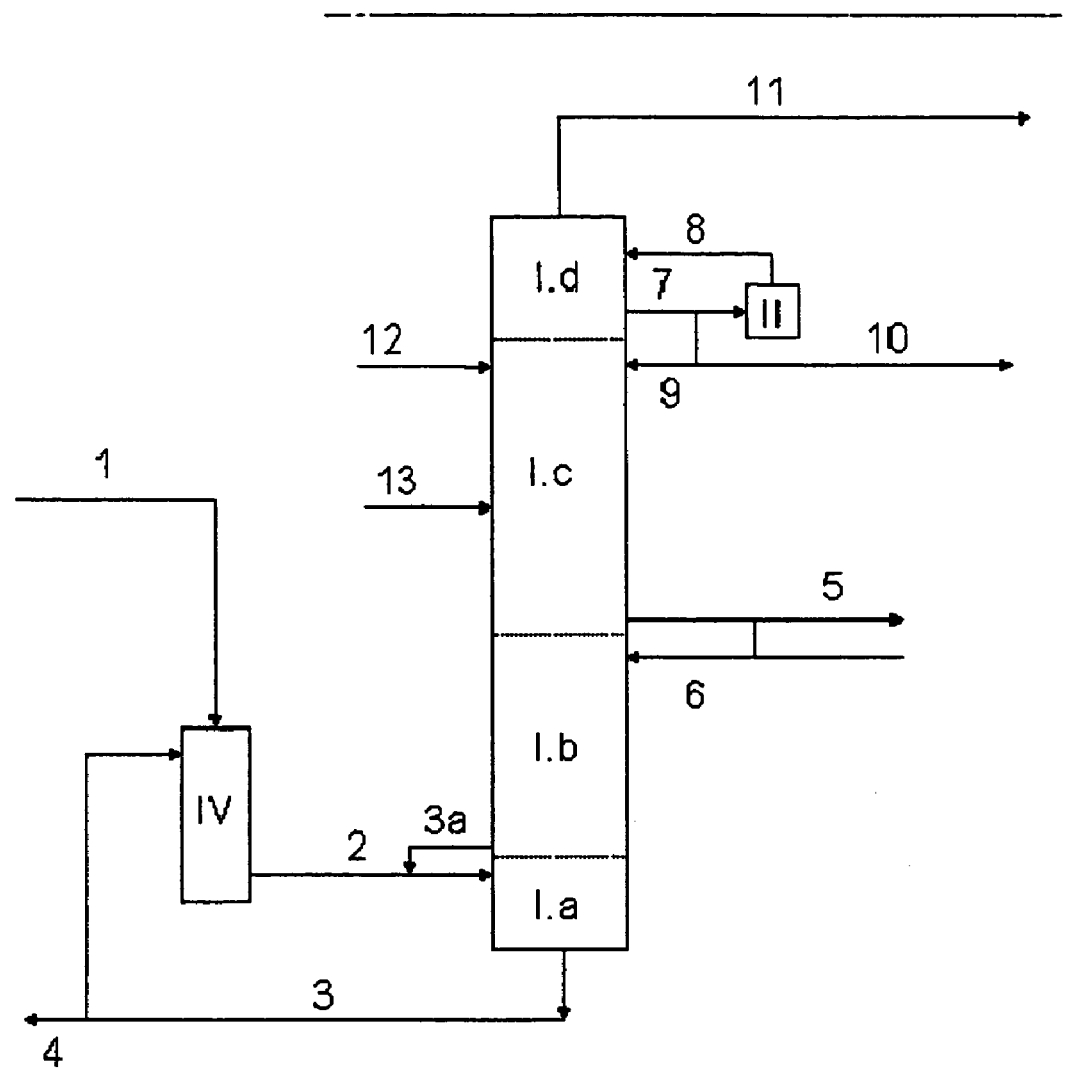
FIG. 4 shows the embodiment of FIG. 1, but in the absence of heat exchanger III.
Figure 5:
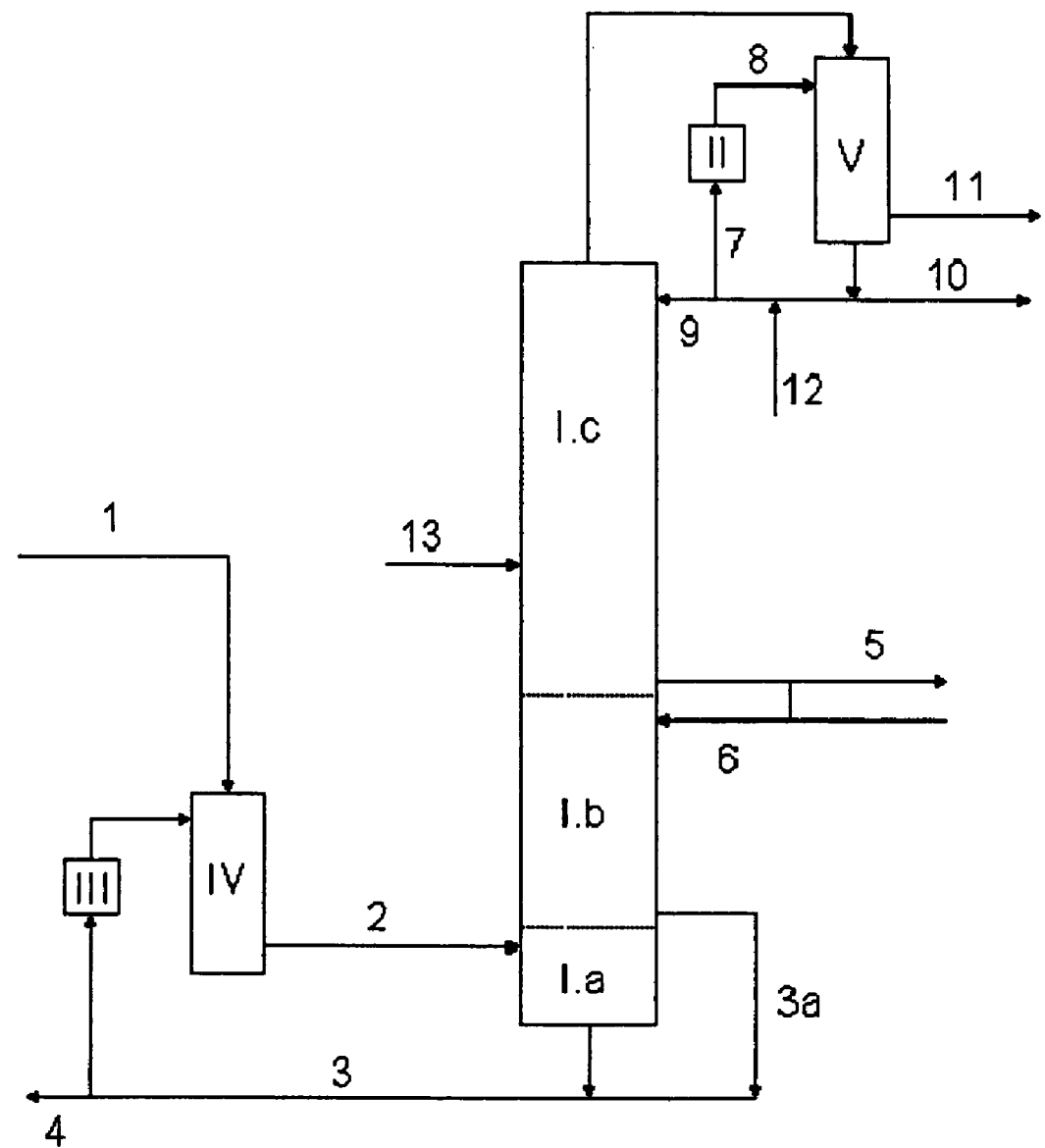
FIG. 5 shows an embodiment of fractional condensation of a hot gas mixture comprising acrylic acid wherein cooling may take place isolated from the column I in a separate apparatus represented by heat exchanger II and external quench (spray cooler) V.

Depending on the separation task, it may also be possible to do without the heat exchanger III (FIG. 3 and FIG. 4).

The cooled product gas mixture which is passed into the lowermost region Ia of a distillation column equipped with internals is separated by fractional condensation into one or more low-boiler, medium-boiler and high-boiler fractions, which are removed via sidestream takeoffs on the respective column sections.

The operating pressure in the column is generally from 0.5 to 5 bar (absolute), frequently from 0.5 to 3 bar (absolute) and in many cases from 0.5 to 2 bar (absolute).

Useful column internals include in principle all conventional internals, in particular trays, packings and/or bubbled packings. Among the trays, preference is given to bubble cap trays, sieve trays, valve trays, Thormann trays and/or dual flow trays. Typically, the total number of trays in a tray column is from 20 to 80, preferably from 50 to 80.

The possibility also exists of adding further cooling circuits to the column. To this end, liquid is withdrawn from the column by means of a collecting tray, this liquid is cooled by means of a suitable heat exchanger and cooled liquid is fed back into the column above the takeoff point (not shown in the figures).

It will be appreciated that a suitable diluent may also be used in the heat exchanger/cooling quench system III/IV. Useful diluents include polar solvents which are inert under the reaction conditions having a boiling point and melting point between 180° C. and 320° C. at atmospheric pressure. Preference is given to ethylhexanoic acid, diphenyl ether, nonylphenol and dibutylformamide. The diluent can be recovered by distillative workup of the discharged high-boiler fraction (stream 4) and recycled. If necessary, commercial dispersing assistants may be added to the high-boiler fraction in the heat exchanger/cooling quench system III/IV. Useful dispersing assistants may be anionic, cationic or nonionic.

In the lowermost column region (Ia, the region below the high-boiler takeoff), there is virtually no condensation of the high-boilers (except on any cooled bridges).

The discharged quenching liquid (stream 4) can be advantageously subjected to thermal and/or catalytic dissociation to dissociate those products of value that are dissociable back to their starting materials, for example acrylic acid oligomer to acrylic acid monomer, in a known manner. The dissociation products are advantageously introduced back into the quench or the column.

Preference is given to subjecting the discharged quenching liquid (stream 4) to thermal treatment. The thermal treatment is usually carried out at from 170 to 190° C. and a pressure of from 300 to 900 mbar. The residence time is typically from 1 to 10 hours. The dissociation products, after removal, are advantageously introduced back into the quench or the column. The residence time is preferably determined by the viscosity of the dissociation residue so that the dissociation residue remains pumpable at the output temperature. Particular preference is given to discharging the dissociation residue at regular intervals and diluting it with from 10 to 30% of a suitable diluent, for example methanol. The pour point of the diluted dissociation residue is customarily from 20 to 50° C.

The crude acrylic acid withdrawn as a medium-boiler in the sidestream (stream 5) generally comprises, as well as acrylic acid,

| | |
|---|---|
| from 0.1 to 2% by weight | of lower carboxylic acids, for example acetic acid |
| from 0.5 to 5% by weight | of water |
| from 0.05 to 1% by weight | of low molecular weight aldehydes |
| from 0.01 to 1% by weight | of maleic acid and/or maleic anhydride |
| from 1 to 500 ppm by weight | of stabilizer, | based in each case on the weight of the crude acrylic acid.

The crude acrylic acid withdrawn as a medium-boiler fraction (stream 5) may either be esterified directly or, for the purposes of further purification, fed to a crystallization step while, in this case, the resulting mother liquor is advantageously fed back into the column as reflux (below the takeoff of the medium-boiler fraction, stream 6).

Such a crystallization step is generally carried out without addition of a solvent, in particular without addition of an organic solvent. The crystallization process to be employed is subject to no restriction. The crystallization may be carried out continuously or batchwise, in one or more steps to almost any desired degree of purity. If required, water may be added prior to crystallization to the crude acrylic acid to be purified by crystallization (up to 10% by weight or more, preferably up to 5% by weight, based on the amount of acrylic acid present). Such addition facilitates the removal of low carboxylic acids, e.g. acetic acid, which are contained in the crude acrylic acid as a by-product, since these are incorporated into the acrylic acid crystals to a slight extent in the presence of water. Also, the presence of water reduces the tendency to encrustation in the crystallizer.

Depending on the separation task, the possibility also exists of using a portion of the crude acrylic acid withdrawn as the medium-boiler fraction as an additional reflux in column section I.b (stream 6).

The low-boiler fraction of the column may be cooled indirectly, for example using heat exchangers, which are known per se to those skilled in the art and are subject to no restriction, or directly, for example using a quench, and preferably by direct cooling.

The cooling may take place isolated from the column in a separate apparatus (see FIG. 5) or else in the top region of column I.d, as shown in FIG. 1. In this case, the condensed low-boiler fraction from column region I.d (stream 7) is generally introduced into the cooler II at a temperature of from 50 to 100° C.

Indirect cooling of the condensed low-boiler fraction may be effected using any conventional heat transferor or heat exchanger. Preference is given to tube bundle heat exchangers, plate heat exchangers or air coolers. The temperature of the condensed low-boiler fraction after leaving the heat exchanger II is normally from 20 to 60° C., frequently from 20 to 35° C. Useful coolants include air for an appropriate air cooler and cooling liquids, in particular water, for other cooling devices.

It will be appreciated that for the purposes of an integrated heat system, the heat of condensation of the low-boiler fraction may even be used completely or partially for melting acrylic acid crystals in a crystallization step or for vaporizing liquid propene upstream of the reactors to produce the hot, acrylic acid-containing gas mixture.

The low-boiler fraction (stream 7, dilute acid) may be partially recycled to the top of the column (stream 8), partially used as reflux for the column section I.c (stream 9) and partially discharged (stream 10). In the case of acrylic acid preparation, it generally comprises:

| | |
|---|---|
| from 80–95% by weight | of water |
| from 2–15% by weight | of acetic acid |
| from 1–5% by weight | of acrylic acid |
| from 0.05–1% by weight | of lower aldehydes (e.g. acrolein, formaldehyde) |

The portion of low-boiler fraction which is recycled to the top of the column is customarily controlled in such a way that uniform gas and liquid loading of the separating internals of the column and optimal material separation are ensured. Preference is given to using "modal" temperature control: for this purpose, three temperature measuring points (giving the corresponding temperatures T1, T2 and T3) are installed in the region of a marked temperature or concentration jump. A value obtained from the three temperature measuring points, for example (T1−2×T2+T3), may be used as the quantity for the column reflux. Also, conductivity control is possible instead of "modal" temperature control.

Advantageously, the low-boilers may also be condensed in an external quench V (FIG. 5) which is operated with dilute acid. In principle, this quenching system may also be configured as described for quenching system IV.

The uncondensable constituents of the product gas mixture (nitrogen, oxygen, propane, propene, or isobutane, isobutene, carbon monoxide, carbon dioxide, etc.) are discharged at the top of the column (stream 11) or preferably, optionally after purification, at least partially recycled into the gas phase oxidation as circuit gas. Particular preference is given to heating stream 11 to from 4 to 10° C. above the top temperature of the distillation column which prevents possible condensation in the offgas or circuit gas pipes.

The temperature at the base of the column is typically from 90 to 130° C., whereas the top temperature is normally from 50 to 100° C., frequently from 60 to 70° C.

The withdrawal temperature of the crude acrylic acid (stream 5) is usually from 80 to 110° C. The crude acrylic acid is cooled to from 14 to 20° C. and, if desired, fed into a crystallizer. The mother liquor from such a crystallization is prewarmed to from 85 to 95° C. and fed back into the column (stream 6). It will be appreciated that the heat from stream 5 may be used to prewarm stream 6 (integrated energy system). Particular preference is given to using the already cooled stream 5 to melt the acrylic acid crystals obtained in the crystallizer. The heat exchangers used for this purpose are subject to no restrictions.

The recycling temperature of the dilute acid (stream 8) into the column is generally from 20 to 35° C.

The columns usable for fractional condensation are subject to no particular restrictions. In principle, all columns having separating internals are suitable.

The column comprises at least one cooling device. For this purpose, all heat transferors or heat exchangers which indirectly (externally) remove the heat liberated during condensation are suitable. For this purpose, all conventional apparatus may be used, and preference is given to using tube bundle heat exchangers, plate heat exchangers and air coolers. Useful coolants for air coolers are correspondingly air and for further cooling devices are cooling liquids, in particular water. When only one cooling device is provided, it is preferably installed at the top of the column where the low-boiler fraction is condensed. Those skilled in the art can easily determine the number of cooling devices required depending on the desired purity of the condensed fractions and hence of the components, while the purity of the condensed components is substantially determined by the installed separation performance of the column, i.e. the column height, diameter and the energy introduced via the gas mixture to be condensed. When a plurality of cooling devices are present, they are conveniently installed in different sections of column. For example, a hot gas mixture which, as well as the high fraction of noncondensable components, comprises at least one high-boiler, at least one medium-boiler and at least one low-boiler fraction may be provided with a cooling device in the lower section of the column to condense the high-boiler fraction and a cooling device at the top of the column to condense the low-boiler fraction. The condensed fractions are withdrawn from the respective sections of the column, preferably via sidestream takeoffs or collecting trays. Depending on the number of components in the high-boiler, medium-boiler and low-boiler fractions, a plurality of sidestream takeoffs may be provided. The fractions withdrawn via the sidestream takeoffs may then be subjected to further purification steps, for example, distillative or extractive separating processes or crystallization, depending on the nature of the secondary components and desired purity of the components. In a preferred embodiment of the invention, a high-boiler takeoff, a low-boiler takeoff and 1 or 2 medium-boiler takeoffs are provided.

The pressure present in the column depends on the quantity of noncondensable components and is generally from 0.5–5 bar absolute, frequently from 0.5–3 bar absolute and in many cases from 0.5–2 bar absolute. The exact operating conditions for the column, such as temperature and pressure, connection and arrangement of the cooling device or devices, arrangement of the sidestream takeoffs for withdrawing the desired fractions, the choice of column height and column diameter, the number and spacing of the separating internals/trays in the column or the type of the separating column internals, may be determined by those skilled in the art on the basis of experiments customary in the field and depending on the separation task.

The sidestream takeoff for the high-boiler fraction is mounted at the lowermost collecting tray, whose design is not restricted, of the column. If desired, a plurality of collecting trays may also be used for a plurality of high-boiler takeoffs which, with the exception of the lowermost collecting tray, may have suitable overflow devices.

The process according to the invention is advantageously carried out in the presence of stabilizers of acrylic acid which are known per se.

For the purposes of this document, stabilizers are such compounds which delay and/or inhibit the polymerization of acrylic acid.

Examples of useful stabilizers include phenolic compounds, amines, nitro compounds, phosphorus or sulfur compounds, hydroxylamines, N-oxyls and certain inorganic salts, and also possibly mixtures thereof in the presence or absence of molecular oxygen.

Preference is given to stabilizers such as phenothiazine, N-oxyls or phenolic compounds.

N-oxyls (nitroxyl radicals or N-oxyl radicals, compounds which have at least one >N—O. -group) include, for example, 4-hydroxy-2,2,6,6-tetramethylpiperidine-N-oxyl, 4-oxo-2,2,6,6-tetramethylpiperidine-N-oxyl, 4-acetoxy-2,2, 6,6-tetramethylpiperidine-N-oxyl, 2,2,6,6-tetramethylpiperidine-N-oxyl or 3-oxo-2,2,5,5-tetramethylpyrrolidine-N-oxyl.

Examples of phenolic compounds include alkylphenols, for example o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol or 2,2'-methylenebis(6-tert-butyl-4-methylphenol), 4,4'-oxydiphenyl, 3,4-methylenedioxydiphenol (sesamol), 3,4-dimethylphenol, hydroquinone, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, 2,4-di-tert-butylphenol, 4-tert-butylphenol, nonylphenol [11066-49-2], octylphenol [140-66-9], 2,6-dimethylphenol, bisphenol A, bisphenol F, bisphenol B, bisphenol C, bisphenol S, 3,3',5,5'-tetrabromobisphenol A, 2,6-di-tert-butyl-p-cresol, Koresin® from BASF AG, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-isopropylphenol, 6-isopropyl-m-cresol, n-octadecyl-β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3, 5-di-tert-butyl-4-hydroxybenzyl)isocyanurate, 1,3,5-tris(3, 5-di-tert-butyl-4-hydroxyphenyl)propionyloxyethyl isocyanurate, 1,3,5-tris(2,6-dimethyl-3-hydroxy-4-tert-butylbenzyl) isocyanurate or pentaerythrityl tetrakis[β-(3,5-di-tert-butyl-4-hydroxyphenyl)propionate], 2,6-di-tert-butyl-4-dimethylaminomethylphenol, 6-sec-butyl-2,4-dinitrophenol, Irganox® 565, 1141, 1192, 1222 and 1425 from Ciba Spezialitätenchemie, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediol bis[(3',5'-di-tert-butyl-4'-hydroxyphenyl) propionate], 0,4,8-dioxa-1,11-undecanediol bis[(3',5'-di-tert-butyl-4'-hydroxyphenyl)propionate], 4,8-dioxa-1,11-undecanediol bis[(3'-tert-butyl-4'-hydroxy-5'-methylphenyl) propionate], 1,9-nonanediol bis[(3',5'-di-tert-butyl-4'-hydroxyphenyl)propionate], 1,7-heptanediaminebis[3-(3',5'-di-tert-butyl-4'-hydroxyphenyl)-propionamide], 1,1-methanediaminebis[3-(3',5'-di-tert-butyl-4'-hydroxyphenyl)-propionamide], 3-(3',5'-di-tert-butyl-4'-hydroxyphenyl)propionic acid hydrazide, 3-(3',5'-dimethyl-4'-hydroxyphenyl)propionic acid hydrazide, bis(3-tert-butyl-5-ethyl-2-hydroxyphen-1-yl)methane, bis(3,5-di-tert-butyl-4-hydroxyphen-1-yl)methane, bis[3-(1'-methylcyclohex-1'-yl)-5-methyl-2-hydroxyphen-1-yl]-methane, bis(3-tert-butyl-2-hydroxy-5-methylphen-1-yl) methane, 1,1-bis(5-tert-butyl-4-hydroxy-2-methylphen-1-yl)ethane, bis(5-tert-butyl-4-hydroxy-2-methylphen-1-yl) sulfide, bis(3-tert-butyl-2-hydroxy-5-methylphen-1-yl) sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris[1'-(3",5"-di-tert-butyl-4"-hydroxyphen-1"-yl)meth-1'-yl]-2,4,6-trimethylbenzene, 1,1,4-tris(5'-tert-butyl-4'-hydroxy-2'-methylphen-1'-yl)butane, aminophenols, e.g. para-aminophenol, nitrosophenols, e.g. para-nitrosophenol or p-nitroso-o-cresol, alkoxyphenols, for example 2-methoxyphenol (guajacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)ethanone (acetovanillone), eugenol, dihydroeugenol or isoeugenol, tocopherols, e.g. α-, β-, γ-, δ- and ε-tocopherol, tocol, α-tocopherolhydroquinone, and 2,3-dihydro-2,2-dimethyl-7-hydroxybenzofuran (2,2-dimethyl-7-hydroxycoumarane), quinones and hydroquinones, such as hydroquinone, 2,5-di-tert-butyl hydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, trimethylhydroquinone, 3-methylpyrocatechol, 4-methylpyrocatechol, tert-butylhydroquinone, 4-ethoxyphenol, 4-butoxyphenol, hydroquinone monobenzyl ether, p-phenoxyphenol, 2-methylhydroquinone, 2,5-di-tert-butylhydroquinone, tetramethyl-p-benzoquinone, diethyl-1,4-cyclohexanedione-2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinonediimine, 1,4-benzoquinonedioxime, coerulignone, 3,3'-di-tert-butyl-5,5'-dimethyldiphenoquinone, p-rosolic acid (aurin), 2,6-di-tert-butyl-4-benzylidenebenzoquinone, 2,5-di-tert-amylhydroquinone.

An example of an aromatic amine is N,N-diphenylamine and an example of a phenylenediamine is N,N'-dialkylparaphenylenediamine, where the alkyl radicals may each independently contain from 1 to 4 carbon atoms and be straight-chain or branched, an example of a hydroxylamine is N,N-diethylhydroxylamine, examples of phosphorus compounds include triphenylphosphine, triphenyl phosphite or triethyl phosphite, an example of a sulfur compound is diphenyl sulfide and examples of inorganic salts include perchloride, dithiocarbamate, sulfate, salicylate and acetate salts of copper, anganese, cerium, nickel and chromium.

Preference is given to phenothiazine, p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone or hydroquinone monomethyl ether and also manganese(II) acetate, cerium (III) carbonate and cerium(III) acetate, and particular preference is given to phenothiazine, p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone or hydroquinone monomethyl ether.

Very particular preference is given to hydroquinone monomethyl ether and a mixture of hydroquinone monomethyl ether and phenothiazine.

The way in which the stabilizer is added is not restricted. Each added stabilizer may be added individually or as a mixture, in liquid form or in dissolved form in a suitable solvent, and the solvent itself may be a stabilizer.

The stabilizer may, for example, be added in a suitable formulation at any desired point in the column, to an external cooling circuit or to a suitable reflux stream. Preference is given to adding it directly into the column or into an external cooling circuit.

When a mixture of a plurality of stabilizers is used, these may be introduced independently at different metering points, which were mentioned above, or the same metering point.

When a mixture of a plurality of stabilizers is used, these may also be dissolved independently in different solvents.

The concentration of the stabilizer in the column for each individual substance may be from 1 to 10000 ppm, preferably from 10 to 5000 ppm, more preferably from 30 to 2500 ppm and in particular from 50 to 1500 ppm.

Preference is given to stabilizing the column in the following manner:

The upper column region is stabilized by at least one phenolic compound, preferably hydroquinone monomethyl ether. Stabilizer is added according to the invention as a melt into the upper part of column section I.c (FIG. 1, stream 12), preferably at the uppermost tray, and/or into the quench circuit I.d/II (not shown) at a concentration of from 50–2500 ppm, preferably from 200–1500 ppm, based on the stream in which the stabilizer is metered in.

Preference is given to a stabilizer mixture in which the melt of at least one stabilizer having a low melting point of, for example, below 120° C., preferably below 100° C., more preferably below 80° C. and in particular below 60° C. serves as solvent for at least one stabilizer having a high melting point of, for example, above 120° C., preferably above 140° C., more preferably above 160° C. and in particular above 180° C.

Particular preference is given to dissolving at least one further stabilizer, more preferably phenothiazine, in the melt in a concentration of from 1–20% by weight, preferably from 5–10% by weight, based on the melt.

It will be appreciated that water-soluble stabilizers may additionally be metered separately into the upper portion of column section I.c or into the quench circuit I.d/II as aqueous solutions.

The remaining column region may be stabilized by a from 0.1–1.5% by weight solution of phenothiazine in acrylic acid, and preference is given to adding it in the column region where the acrylic acid concentration is from 5–20%, preferably from 12–18%, and the water concentration is from 40–95%, preferably from 40 to 60% (stream 13). The quantity added is determined in such a way that the phenothiazine content in the acrylic acid fraction (medium-boiler fraction, stream 5) is from 10–1000 ppm, preferably from 50–500 ppm.

The "upper column region" mentioned is the region above the column region where the acrylic acid and water are present in the concentrations mentioned.

The stabilizer solutions or stabilizer melts may be metered in using pumps. For stabilizer melts, preference is given to pressurized receivers. For instance, a hydroquinone monomethyl ether/phenothiazine melt may be forced directly from the melting and receiving vessel via a regulating valve into the column. To this end, a suitable gas, for example a nitrogen-containing gas, such as nitrogen, air or air/nitrogen mixtures, is injected into the vessel and pressurized to the desired pressure. Preference is given to pressures of from 2 to 10 bar. Particular preference is given to using a buffer vessel which takes over the supply of the stabilizer when the melting and receiving vessel is filled. The vessels, valves, pumps or pipes may each be trace heated, in order to prevent solidification of the melt.

The quench IV in which the hot product gas mixture of the oxidation reaction is cooled to from 100–180° C. generally requires no additional stabilization.

The surfaces in the column which are sparingly wetted are generally sprayed with stabilizing liquid. Preference is given to spraying in a portion of liquid withdrawn from the collecting trays (for example, stream 5) above the collecting trays to provide additional wetting thereof. Particular preference is given to spraying a portion of the reflux below the collecting trays against their undersides for wetting of the same.

It has to be considered surprising that phenolic compounds, particularly hydroquinone monomethyl ether, are a good solvent for phenothiazine. Up to a melting temperature of 100° C., up to about 20% of phenothiazine may be dissolved. Despite the low solubility of phenothiazine in dilute acid, the stabilization according to the invention does not lead to solid deposits or blockages by phenothiazine in the upper column region.

The invention also provides melts comprising
a) at least one phenolic compound,
b) phenothiazine and
c) optionally at least one further compound which is effective as a stabilizer.

Typical melts according to the invention have the following composition:
a): 60–99% by weight, preferably 80–95% and more preferably 90–95%,
b): 1–20% by weight, preferably 5–15% and more preferably 5–10% and
c): 0–20% by weight, preferably 0–15%, more preferably 0–5% and most preferably 0%, where the sum thereof is always equal to 100% by weight.

Preference is given to such melts where c) is selected from the group consisting of the above-recited N-oxyl compounds and inorganic salts, more preferably the N-oxyl compounds.

Particular preference is given to such melts where the phenolic compounds a) are selected from the group consisting of the above-recited phenolic compounds, most preferably from the group consisting of p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone and hydroquinone monomethyl ether. In particular, compound a) is hydroquinone monomethyl ether.

The melting point of the melts according to the invention is generally 100° C. or lower, and preference is given to those having a melting point of 80° C. or lower and very particular preference to those having a melting point of 60° C. or lower.

The invention also provides the use of the melt according to the invention for stabilizing ethylenically unsaturated compounds in processes for preparing them, for example, styrene, acrylonitrile, vinyl acetate, vinyl chloride, butadiene, isoprene or chloroprene, preferably α,β-ethylenically unsaturated carbonyl compounds such as acrylic acid, methacrylic acid, acrolein, methacrolein, crotonic acid, maleic acid, maleic anhydride, methyl methacrylate, methyl acrylate, ethyl acrylate, butyl acrylate or 2-ethylhexyl acrylate, more preferably acrylic acid, methacrylic acid, acrolein or maleic anhydride, most preferably acrylic acid or methacrylic acid, and in particular acrylic acid.

The process according to the invention facilitates a more economically viable workup of acrylic acid by reducing the effort associated with the preparation of the stabilizer batches and also improves stabilization in the upper column region, which leads to a higher yield and longer running time of the column and accordingly reduced downtime.

The present invention further provides a process for rectificatively separating substance mixtures comprising at least one polymerizable compound in the presence of a stabilizer composition comprising at least one phenolic stabilizer, wherein the stabilizer composition is metered into the rectification unit as a melt.

Polymerizable compounds are ethylenically unsaturated compounds, preferably those ethylenically unsaturated compounds which can polymerize by a free radical polymerization mechanism. Examples include esters of (meth)acrylic acid with alcohols which have from 1 to 20 carbon atoms, for example methyl(meth)acrylate, ethyl(meth)acrylate, n-butyl(meth)acrylate and 2-ethylhexyl (meth)acrylate, vinylaromatic compounds, for example styrene, divinylbenzene, α,β-unsaturated nitriles, for example acrylonitrile and methacrylonitrile, α,β-ethylenically unsaturated aldehydes, for example acrolein and methacrolein, vinyl esters, for example vinyl acetate and vinyl propionate, halogenated ethylenically unsaturated compounds, for example vinyl chloride and vinylidene chloride, conjugated unsaturated compounds, for example butadiene, isoprene and chloroprene, monounsaturated compounds, for example ethylene, propylene, 1-butene, 2-butene and isobutene, cyclic monounsaturated compounds, for example cyclopentene, cyclohexene and cyclododecene, N-vinylformamide, allylacetic acid, vinylacetic acid, monoethylenically unsaturated carboxylic acids having from 3 to 8 carbon atoms and also their water-soluble alkali metal, alkaline earth metal or ammonium salts, for example: acrylic acid, methacrylic acid, dimethacrylic acid, ethacrylic acid, maleic acid, citraconic acid, methylmalonic acid, crotonic acid, fumaric acid, mesaconic acid and itaconic acid, maleic acid, N-vinylpyrrolidone, N-vinyllactams, for example N-vinylcaprolactam, N-vinyl-N-alkyl-carboxamides or N-vinylcarboxamides, for example N-vinylacetamide, N-vinyl-N-methylformamide and N-vinyl-N-methylacetamide, vinyl ethers, for example methyl vinyl ether, ethyl vinyl ether, n-propyl vinyl ether, isopropyl vinyl ether, n-butyl vinyl ether, sec-butyl vinyl ether, isobutyl vinyl ether, tert-butyl vinyl ether and 4-hydroxybutyl vinyl ether, and vinylphosphonic acid and also mixtures thereof.

Preference is given to (meth)acrylic esters, vinylaromatic compounds, halogenated ethylenically unsaturated compounds, monoethylenically unsaturated carboxylic acids and vinyl ethers, particular preference to (meth)acrylic esters, vinylaromatic compounds and monoethylenically unsaturated carboxylic acids, very particular preference to (meth)acrylic esters and monoethylenically unsaturated carboxylic acids and in particular to monoethylenically unsaturated carboxylic acids.

Substance mixtures comprising polymerizable components are those in which at least 50% by weight of the components which are liquid at room temperature (25° C.) are polymerizable components, preferably at least 60% by weight, more preferably at least 75% by weight, most preferably at least 85% by weight and in particular at least 90% by weight.

Rectificative separation may mean a fractional condensation of a substantially gaseous feed or a distillation of a substantially liquid feed. The rectificative separation may be effected in a separating column having, for example, from 1 to 150 theoretical plates, preferably from 2 to 120, more preferably from 5 to 100, most preferably from 10 to 80 and in particular from 20 to 50, theoretical plates.

The rectification units are of designs known per se and have the customary internals. Useful column internals include in principle any common internals, for example trays, structured packings and/or dumped packings. Among the trays, preference is given to model cap trays, sieve trays, valve trays, Thormann trays and/or dual-flow trays, and among the dumped packings, preference is given to those having rings, spirals, saddles, Raschig rings, Intos rings or Pall rings, barrel or Intalox saddles, Top-Pak, etc., or braids.

The rectification units generally have at least one condenser of customary design, for example a direct or indirect condenser, preferably a tube or plate heat exchanger or quench cooler, and distillation units additionally have at least one evaporator of customary design, for example a tube bundle, plate, thin-film or falling-film evaporator.

The bottom and top temperatures and pressures depend on the polymerizable compound to be separated. In general, operation is effected at reduced pressure in order to reduce the distillation temperature, but rectification may also be carried out at elevated pressure in the case of volatile compounds.

Examples of top temperatures and pressures are given for the following polymerizable compounds:

|  | Top temperature [° C.] | Top pressure [° C.] |
|---|---|---|
| Styrene | 50–150 | 50–1013 |
| Vinyl acetate | 30–80 | 200–1013 |
| Acrylonitrile |  |  |
| Vinyl propionate | 50–100 | 200–1013 |
| Methyl vinyl ether | −30–+10 | 500–2000 |
| Ethyl vinyl ether | 0–40 | 500–2000 |
| 4-Hydroxybutyl vinyl ether | 80–190 | 50–1013 |
| Methacrylic acid | 80–160 | 100–1013 |
| Methyl methacrylate | 50–100 | 100–1013 |
| Acrylic acid | 60–140 | 50–1013 |
| Methyl acrylate | 30–80 | 50–1013 |
| Ethyl acrylate | 40–100 | 50–1013 |
| Butyl acrylate | 70–150 | 50–1013 |
| 2-Ethylhexyl acrylate | 80–200 | 50–1013 |

Depending on the number of theoretical plates, the bottom temperature in each case will generally be from 10 to 50° C. higher than the top temperature.

Stabilizer compositions are those in which at least 50% by weight of the composition is active as a stabilizer against polymerization, preferably free radical polymerization, of the polymerizable compound to be stabilized, preferably at least 65% by weight, more preferably at least 75% by weight, most preferably at least 90% by weight and in particular 100% by weight.

The melting point of such a stabilizer composition is preferably above 0° C. and more preferably above 250° C. The melting point of such a stabilizer composition is, for example, below 100° C., preferably below 80° C. and more preferably below 600° C.

The stabilizer compositions comprise, for example, at least one of the above-cited phenolic compounds, preferably p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone or hydroquinone monomethyl ether, more preferably 2-tert-butylphenol, 4-tert-butylphenol, 2,4-di-tert-butylphenol, 2-methyl-4-tert-butylphenol, 4-tert-2,6-dimethylphenol, hydroquinone or hydroquinone monomethyl ether, and the stabilizer compositions most preferably comprise one of the above-cited melts according to the invention, and in particular, the stabilizer composition is one of the above-cited melts according to the invention.

The stabilizer composition may be metered in as a melt at any desired point in the rectification unit, including the lines and devices connected to it, for example condensers, evaporators or vacuum units, and preference is given to metering it in to the upper half (based on the number of separating internals) of the column, particular preference to metering it into the upper third, very particular preference to metering it into the upper quarter and in particular into the upper tenth, especially onto the uppermost tray. In a further preferred embodiment, the molten stabilizer composition is added to the reflux stream and fed with it into the upper section of the column.

The ppm and percentage values reported in this document refer, unless otherwise stated, to ppm by weight and percentage by weight.

The process according to the invention is illustrated by the following example:

INVENTIVE EXAMPLE (FIG. 5)

The heterogeneously catalyzed gas phase oxidation gave a product mixture (stream 1) at 270° C. having the following composition:

| 11.5% by weight | of acrylic acid |
|---|---|
| 0.28% by weight | of acetic acid |
| 27 ppm by weight | of propionic acid |
| 0.093% by weight | of maleic anhydride |
| 0.1% by weight | of acrolein |
| 0.1% by weight | of formaldehyde |
| 31 ppm by weight | of furfural |
| 25 ppm by weight | of benzaldehyde |
| 0.29% by weight | of propene |
| 3.8% by weight | of oxygen |
| 5.2% by weight | of water |
| 2.8% by weight | of carbon oxides, and the remainder $N_2$ |

The product mixture (3600 g/h) was cooled in a spray cooler (IV) to a temperature of 121° C. The sprayer liquid used was the high-boiler fraction (stream 3) withdrawn from the separating column via a collecting tray. The sprayer liquid was circulated through the tube bundle heat exchanger (III) operated with heat-transfer oil. 43 g/h of low-boilers were continuously withdrawn from the circuit (stream 4).

The product mixture (3600 g/h) was cooled in a spray cooler (IV) to a temperature of 121° C. The sprayer liquid used was the high-boiler fraction (stream 3) withdrawn from the separating column via a collecting tray. The sprayer liquid was circulated through the tube bundle heat exchanger (III) operated with heat-transfer oil. 43 g/h of low-boilers were continuously withdrawn from the circuit (stream 4).

The high-boilers (stream 4) were collected. The oligomeric acrylic acids contained therein were dissociated batchwise in a stirred vessel to give products of value (not shown). The dissociation was carried out at 190° C. and a pressure of 500 mbar. The dissociation residue was diluted with 25% by weight of methanol and disposed of. The dissociation distillate was collected and continuously introduced into the quench circuit (III/IV). 34 g/h of dissociation distillate were recycled. The dissociation distillate comprised from 0.5–1.0% by weight of hydroquinone monomethyl ether and did not have to be additionally stabilized.

The product gas mixture cooled to a temperature of 121° C. was introduced into the separating column below the collecting tray (column region Ia).

The column was a tray column having 45 dual flow and 40 bubble cap trays. The tray above tray 15 was configured as a further collecting tray. 1680 g/h of crude acrylic acid at a temperature of 101° C. were discharged via this tray and had the following composition (stream 5):

| acrylic acid | 97% by weight |
|---|---|
| acetic acid | 0.6% by weight |
| propionic acid | 640 ppm by weight |
| furfural | 0.4% by weight |
| maleic anhydride | 0.14% by weight |
| benzaldehyde | 550 ppm by weight |
| water | 1.5% by weight |

The crude acrylic acid was introduced to a suspension crystallizer.

In addition, 620 g/h of crude acrylic acid were introduced as an additional reflux to tray 15.

At the top of the column, a gaseous mixture was withdrawn and subjected in spray cooler (V) to partial condensation. 482 g/h of the resulting dilute acid which consists essentially of 5.5% by weight of acrylic acid, 5.2% by weight of acetic acid and 85% by weight of water were recycled into the top of the column at a temperature of 30° C. (stream 9). 114 g/h of the dilute acid were continuously withdrawn (stream 10).

A solution of 5% by weight of phenothiazine in hydroquinone monomethyl ether was introduced as a melt (at a temperature of 60° C.) into the quench circuit at a rate of 0.5 g/h (stream 12).

A solution of 0.5% by weight of the phenothiazine in acrylic acid was introduced at a rate of 18 g/h to the 47$^{th}$ tray of the separating column (stream 13).

The crystallizer was a stirred vessel (3 1 capacity) equipped with a helical stirrer. The heat of crystallization was removed via the jacket of the vessel. The equilibrium temperature of the solution was 9.7° C. The suspension resulting from the crystallization (solids content about 30% by weight) was separated batchwise into crystals and mother liquor on a centrifuge at 2000 rpm (centrifuge diameter 300 mm) and a spinning time of 1 min. The crystals were then washed with melted (previously washed) crystals (134 g/h) for 1 min at 2000 rpm. The mother liquor together with the washing liquid was recycled to the 15$^{th}$ tray of the separating column (stream 6).

The analysis of the washed crystals (537 g/h) gave the following composition:

| | |
|---|---|
| acrylic acid | 99.7% by weight |
| acetic acid | 0.14% by weight |
| propionic acid | 230 ppm by weight |
| maleic anhydride | 72 ppm by weight |
| furfural | 210 ppm by weight |
| benzaldehyde | 28 ppm by weight |
| water | 0.11% by weight |

Even after a running time of 1200 hours, the separating device described showed negligible polymer formation.

COMPARATIVE EXAMPLE

Example 2 of the German patent application 100 53 086.9 of 26.10.2000 was repeated. After a running time of 1200 hours, the process was shut down and distinct deposits owing to polymer formation were noticeable.

We claim:

1. A process for the fractional condensation of a hot gas mixture comprising acrylic acid and at least one further condensable component in a column in the presence of at least one stabilizer, which comprises metering in at least a portion of the at least one stabilizer as a melt.

2. A process as claimed in claim 1, wherein the melt of at least one stabilizer having a melting point below 120° C. is used as a solvent for at least one stabilizer having a melting point above 120° C.

3. A melt comprising
   a) at least one phenolic compound, and
   b) phenothiazine,
   wherein said melt has a melting point of greater than 250° C.

4. The melt as claimed in claim 3, wherein a) is selected from the group consisting of p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone and hydroquinone monomethyl ether.

5. The melt as claimed in claim 3 which comprises the following composition:
   a): 60–99% by weight, and
   b): 1–20% by weight
   wherein the sum thereof is equal to 100% by weight.

6. A process as claimed in claim 1, wherein said metering comprises introducing the melt comprising a) at least one phenolic compound, b) phenothiazine and c) optionally at least one compound which is effective as a stabilizer into the upper column region and introducing phenothiazine into the remaining column region.

7. A process as claimed in claim 1, wherein the hot gas mixture is cooled in an apparatus isolated from the column.

8. A process as claimed in claim 1, wherein at least one discharged stream is subjected to a thermal and/or catalytic treatment.

9. A process as claimed in claim 1 which is carried out in the presence of molecular oxygen.

10. A method of stabilizing ethylenically unsaturated compounds in processes for preparing the ethylenically unsaturated compounds which comprises
    incorporating the melt as claimed in claim 3 into a medium comprising the ethylenically unsaturated compound.

11. A process for rectificatively separating substance mixtures comprising at least one polymerizable compound in the presence of a stabilizer composition comprising at least one phenolic stabilizer, which comprises metering the stabilizer composition into a rectification unit as a melt.

12. The melt as claimed in claim 3, wherein said melt further comprises at least one stabilizer, wherein said stabilizer delays or inhibits polymerization of acrylic acid.

13. The melt as claimed in claim 12, wherein said stabilizer is present in a concentration of up to 20% by weight.

14. The melt as claimed in claim 12, wherein said stabilizer is selected from the group consisting of a phenothiazine, an N-oxyl, and a phenolic compound.

15. A melt comprising
    a) at least one phenolic compound, and
    b) at least 5% by weigh of phenothiazine.

16. The melt as claimed in claim 15, wherein a) is selected from the group consisting of p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone and hydroquinone monomethyl ether.

17. The melt as claimed in claim 15 which comprises the following composition:
    a): 60–99% by weight, and
    b): 5–20% by weight,
    wherein the sum thereof is equal to 100% by weight.

18. The melt as claimed in claim 15, wherein said melt further comprises at least one stabilizer, wherein said stabilizer delays or inhibits polymerization of acrylic acid.

19. The melt as claimed in claim 18, wherein said stabilizer is present in a concentration of up to 20% by weight.

20. The melt as claimed in claim 18, wherein said stabilizer is selected from the group consisting of a phenothiazine, an N-oxyl, and a phenolic compound.

21. The melt as claimed in claim 3, wherein said melt has a melting point of greater than 25° C. and less than 100° C.

22. The melt as claimed in claim 3, wherein said melt has a melting point of greater than 25° C. and less than 80° C.

23. The melt as claimed in claim 3, wherein said melt has a melting point of greater than 25° C. and less than 60° C.

* * * * *

UNITED STATES PATENT AND TRADEMARK OFFICE
CERTIFICATE OF CORRECTION

| | | |
|---|---|---|
| PATENT NO. | : 7,109,328 B2 | |
| APPLICATION NO. | : 10/500009 | |
| DATED | : September 19, 2006 | |
| INVENTOR(S) | : Ulrich Hammon et al. | |

It is certified that error appears in the above-identified patent and that said Letters Patent is hereby corrected as shown below:

Column 15, lines 60-61, " wherein said melt has a melting point of greater than 250°C." should read -- wherein said melt has a melting point of greater than 25°C. --.

Signed and Sealed this

Twentieth Day of November, 2007

JON W. DUDAS
*Director of the United States Patent and Trademark Office*